(12) United States Patent
Huang et al.

(10) Patent No.: US 7,407,665 B2
(45) Date of Patent: Aug. 5, 2008

(54) SKIN CARE COSMETIC COMPOSITIONS AND METHODS FOR MICROEMULSIFICATION OF SEBUM ON CONTACT

(75) Inventors: Lei Huang, North Arlington, NJ (US); Carlos Co, Cincinnati, OH (US); Alexander Lips, Edgewater, NJ (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 702 days.

(21) Appl. No.: 10/648,695

(22) Filed: Aug. 27, 2003

(65) Prior Publication Data

US 2005/0048025 A1 Mar. 3, 2005

(51) Int. Cl.
*A61Q 19/00* (2006.01)
(52) U.S. Cl. .................................. 424/401; 424/78.03
(58) Field of Classification Search .................. None
See application file for complete search history.

(56) References Cited

U.S. PATENT DOCUMENTS

| 5,540,853 | A | * | 7/1996 | Trinh et al. .................. 510/101 |
| 5,858,954 | A | | 1/1999 | Balzer |
| 6,191,090 | B1 | | 2/2001 | Mondin et al. |
| 6,303,662 | B1 | | 10/2001 | Nagahama et al. |

FOREIGN PATENT DOCUMENTS

WO 02/102327 12/2002

OTHER PUBLICATIONS

International Search Report, PCT/EP2004/008660, mailed on Oct. 28, 2004—2 pp.
S. Jain & F. S. Bates, "On the Origins of Morphological Complexity in Block Copolymer Surfactants," Science, vol. 300, Apr. 18, 2003, pp. 460-464, XP00230179.
Strey, R. "Microemulsion microstructure and interfacial curvature", *Colloid & Polymer Science* 272: 1005-1019 (1994).
Silas, J.A. et al. "the Phase Behavior and microstructure of Efficient Cationic-Nonionic Microemulsions", *J. of Colloid and Interface Science* 243, 248-254 (2001).
Kunieda, H et al., "Mixing of Nonionic Surfactants at Water-Oil Interfaces in Microemulsions", *Langmuir* 9, 3345-3351 (1993).
Graciaa, A. et al., "Improving Solubilization in Microemulsions with Additives. 1. The Lipophilic Linker Role", *Langmuir* 9, 669-672 (1993).
Graciaa, A. et al., "Improving Solubilization in Microemulsions with Additives. 2. Long Chain Alcohols as Lipophilic Linkers", *Langmuir*, 9, 3371-3374, (1993).
Minana-Perez, M., et al., "Solubilization of polar oils with extended surfactants" *Colloids and Surfaces*, 100, 217-224, (1995).
Jakobs, B. et al., "Amphiphilic Block copolymers as Efficiency Boosters for Microemulsions", *Langmuir*, 15, 6707-6711, (1999).
Endo, H. et. al. "Membrane Decoration by Amphiphilic Block Copolymers in Bicontinuous Microemulsions", *Physical Review Letter*, vol. 85, No. 1, 102-105, (2000).
Downing, D. T., et al., "Synthesis and Composition of Surface Lipids of Human Skin", *J. Invest. Dermatology*, vol. 62, No. 3, 228-244, (1974).
Strauss, J. et al., "Sebaceous Glands in Physiology, Biochemistry and Molecular biology of skin" *Oxford University Press*, New York, (1991).
Downing, D. et. al. "Skin Lipids: An Update", *J. Invest. Dermatology*, vol. 88, 2s-6s, (1987).
Mori, F., et. al. "Phase Behavior, Dynamic Contacting and Detergency in Systems Containing Triolein and Nonionic Surfactants", *Colloids and Surfaces*, 40, 323-345, (1989).
Kunieda, H. et al., "Two Types of Surfactant Phases and Four Coexisting Liquid Phases in a Water/Nonionic Surfactant/Triglyceride/Hydrocarbon System", *J. Phys. Chem.* 92, 185-189, (1988).
Kunieda, H., et al., "Overlapping of Three-Phase Regions in a Water/Nonionic Surfactant/Triglyceride System", *J. of Colloid and Interface Science*, vol. 140, No. 2, 383-390, (1990).
Kahlweit, M. et al., "Search for Tricritical Points in Ternary Systems: Water-Oil-Nonionic Amphiphile", *J. Phys. Chem.*, 90, 671-677, (1986).
Kahlweit, M. et al., "Properties of the Three-Phase Bodies in $H_2O$-Oil-Nonionic Amphiphile Mixtures", *Langmuir*, vol. 4, 785-790, (1988).
Kahlweit, M. et al., "Patterns of the Phase Behavior of Mixtures of $H_2O$, Nonpolar Solvents, Amphiphiles, and Electrolytes", *Langmuir*, vol. 4, No. 3, 499-511, (1988).

* cited by examiner

*Primary Examiner*—Jyothsna A Venkat
(74) *Attorney, Agent, or Firm*—Michael P. Aronson

(57) ABSTRACT

A combination of a non-ionic tri-block poly-propylene-oxide, poly-ethylene-oxide alcohol ether surfactant coupled with block polymer poly(Butadiene-b-Ethylene Oxide) is an excellent surfactant phase to micro-emulsify sebum on contact. A method of micro-emulsification of sebum on contact with inventive compositions according to the present invention will form micro-emulsions which can enhance (1) deep pore cleansing of skin and (2) delivery of skin benefit actives into the skin.

11 Claims, No Drawings

SKIN CARE COSMETIC COMPOSITIONS AND METHODS FOR MICROEMULSIFICATION OF SEBUM ON CONTACT

FIELD OF THE INVENTION

Cosmetic methods and compositions for micro-emulsification of sebum on contact, comprising a tri-block propylene oxide, ethylene oxide surfactant and a poly(Butadiene-b-Ethylene Oxide) polymer in a cosmetic vehicle.

BACKGROUND OF THE INVENTION

Micro-emulsions are thermodynamically stable isotropic dispersions of oil and water containing domains of nanometer dimensions or bi-continuous phases, which are stabilized by the interfacial film of surface active agents. The properties of micro-emulsions make them attractive for cosmetic formulations from several different aspects. Micro-emulsions are transparent (or translucent), giving a perception of a "clean" system, and they form emulsions spontaneously. Micro-emulsions have an ultra-low interfacial tension between oil and water interface, which is key for their formation. This interfacial tension property also makes micro-emulsions potentially better (1) deep pore cleansers, e.g. in wash-off compositions and (2) follicle delivery vehicles, e.g. in leave-on compositions, due to enhanced capillary effects.

It is relatively easy to micro-emulsify short chain oils. On the other hand, bulky oils such as long chain fatty esters and triglycerides, such as those present in skin sebum, are notoriously difficult to be micro-emulsified. The interaction of such high molecular weight oils with surfactants is not well understood in the art and is radically different from that of conventional alkane oils. This is the challenge addressed by the present invention. Specifically, the problem addressed by the present invention is how to micro-emulsify bulky and high molecular weight oils, such as triglycerides in sebum. It is well known that co-surfactants can enhance micro-emulsification efficiency. But the selection of co-surfactant is mainly based on trial-and-error.

Regarding applications in cosmetics, sebum is one of the most important oils related to surfactant-oil interactions on skin. Sebum is a complex mixture of triglycerides(57%), wax esters(26%), squalene (12%), sterol esters (3%) and free sterols (2%) produced by sebocytes (cells of the sebaceous glands in the skin) and secreted to the skin surface. A frequent and undesirable skin condition is "oily skin," the condition which results from the excessive amount of sebum on the skin. Oily skin is associated with a shiny, undesirable appearance and a disagreeable tactile sensation and affects various age groups. Therefore, cosmetic products that obviate the undesirable appearance and disagreeably tactile sensation due to sebum are highly desirable. Additionally, the present invention is based on the discovery that micro-emulsification of sebum on contact with inventive compositions according to the present invention will form micro-emulsions which can enhance (1) deep pore cleansing of skin and (2) deep pore delivery of skin benefit actives through the follicles.

Cleansing into pores presents a considerable technical challenge over and above normal surface cleaning processes due to the difficulty to access the target soil. Also, the nature of the oil is of great importance in determining both the feasibility and rate of removal. Although conventional skin cleansers, such as soap and water, are very effective in removing surface dirt and grease, continuous production of sebum by the sebaceous gland ensures that the re-greasing process begins immediately so that after a relatively short time, the sebum level is reestablished.

Micro-emulsion is an ideal medium for delivery of skin benefit agents into the skin. Applying products that are themselves micro-emulsions has been widely used in a variety of skin care products and delivery vehicles and examples of such products are described in U.S. Pat. Nos. 5,858,954 and 6,303,662, and in PCT Published Application WO 02/102327. Describing micro-emulsifying oils or soils on contact is Mondin, et al., U.S. Pat. No. 6,191,090, relating to a hard surface liquid cleaning composition based on EO—PO nonionic surfactant in combination with other components of the emulsification system described therein.

The art cited above does not suggest or disclose cosmetic compositions or methods for micro-emulsification of sebum on contact of a composition with skin, nor do they suggest or disclose an efficient emulsification system for doing so. Therefore, a need remains for novel cosmetic compositions and methods that make use of natural skin sebum to enhance skin cleansing or to deliver actives to skin from leave-on or wash-off compositions.

SUMMARY OF THE INVENTION

Micro-emulsification of sebum on contact with inventive compositions according to the present invention will form micro-emulsions which can enhance (1) deep pore cleansing of skin and (2) deep pore delivery of skin benefit actives through the follicles. Skin care and cleansing cosmetic methods and compositions for micro-emulsification of skin sebum on contact include, with a cosmetic vehicle:

(i) about 1% to about 40%, preferably about 12% to about 35%, and more preferably about 12% of the composition of a compound of the formula A, a non-ionic, tri-block surfactant that is a poly-propylene-oxide, poly-ethylene-oxide ether of a $C_{4-18}$ alcohol:

$$R\text{—}O\text{—}(PO)_x\text{—}(EO)_y\text{—}H \quad (A)$$ 

where:
R is a linear or branched alkyl or alkenyl chain having about 4 to about 18 carbon atoms;
O is an oxygen atom;
PO is a propylene oxide group;
EO is an ethylene oxide group; and
x an integer between about 5 and about 30;
y is an integer between about 5 and about 30; preferably, the ratio of x:y being about 1:3 to about 3:1; and
H is hydrogen;
about 0.01% to about 1% of poly(Butadiene-b-Ethylene Oxide) polymer;
where the poly-Butadiene chain has a molecular weight of about 1,000 to about 10,000 and the poly-Ethylene Oxide chain has a molecular weight of about 1,000 to about 20,000.

Sebum micro-emulsions can also be formed in the presence of sweat, making it possible to control sensory perception of sebum and sweat simultaneously. The inventive composition may optionally include an astringent salt. Astringent salts include aluminum hydroxide, aluminum halides, aluminum hydroxyhalides, zirconyl oxyhalides, zirconyl hydroxyhalides and mixtures thereof. More generally, aluminum salts have the general formula $Al_2(OH)_xQ_y\text{—}XH_2O$; wherein Q is chlorine, bromine or iodine; wherein x is 2 to 5 and x+y=6 and x and y do not need to be integers; and wherein X is about 1 to about 6. Preferably, the skin care cosmetic compositions include an astringent salt selected from the group consisting of aluminum chloride, aluminum chlorohydrate, aluminum chlorohydrex, aluminum chlorohydrex PEG, aluminum chlorohydrex PG, aluminum dichlorohydrate, aluminum dichlorohydrex PEG, aluminum dichlorohydrex PG, aluminum sesquichlorohydrate, aluminum sesquichlorohydrex PEG, aluminum sesquichlorohydrex PG, aluminum sulfate, aluminum zirconium octachlorohydrate, aluminum zirconium octachlorohydrex GLY, aluminum zirconium pentachlorohydrate, aluminum zirconium pentachlorohydrex GLY, aluminum zirconium tetrachlorohydrate, aluminum zirconium trichlorohydrate, aluminum zirconium tetrachlorohydrate GLY, and aluminum zirconium trichlorohydrate GLY, and mixtures thereof.

The present invention also includes a cosmetic method of reducing or controlling the perception of oily or greasy skin by applying to the skin the inventive composition. A cosmetic method of micro-emulsifying sebum on contact, by applying to the skin the inventive composition is another aspect of the present invention.

DETAILED DESCRIPTION OF THE INVENTION

The present invention addresses the challenge of micro-emulsification of sebum on contact, or in-situ. Micro-emulsification of sebum is useful to enhance (1) deep pore cleansing of skin and (2) follicle delivery of skin benefit actives into the skin. The micro-emulsification takes place upon contact of the inventive compositions with skin sebum. The inventive cosmetic compositions include a tri-block, nonionic, poly-propylene oxide, poly-ethylene oxide surfactant in combination with a poly(Butadiene-b-Ethylene Oxide) polymer within a cosmetically acceptable vehicle.

Except in the operating and comparative examples, or where otherwise explicitly indicated, all numbers in this description indicating amounts of material or conditions of reaction, physical properties of materials and/or use are to be understood as modified by the word "about." All amounts are by weight of the overall composition, unless otherwise specified.

As used herein, the term "comprising" means including, made up of, composed of, consisting and/or consisting essentially of.

The term "skin" as used herein includes the skin on the face, neck, chest, back, arms, hands, legs and scalp.

TRI-BLOCK POLY-PROPYLENE-OXIDE, POLY-ETHYLENE-OXIDE SURFACTANT

The inventive methods and compositions include a nonionic, tri-block surfactant that is a poly-propylene-oxide, poly-ethylene-oxide ether of a $C_{4-18}$ alcohol, and has the general formula A:

$$R\text{—}O\text{—}(PO)_x\text{—}(EO)_y\text{—}H \quad (A)$$

Where:

R is a linear or branched alkyl or alkenyl chain having about 4 to about 18 carbon atoms, preferably 8 carbon atoms for an ideal balance between hydrophobicity and water solubility. In order for the R-group to be sufficiently hydrophobic, R should have a minimum of 4 carbon atoms. The maximum number of carbons in the R-group should not exceed about 18 carbon atoms for partial solubility in water.

O is an oxygen atom.

PO is a propylene oxide group (PO-group). The PO group is relatively hydrophobic and stays in the oil phase in order to form an extended link between oil and water droplets in the microemulsion. Thus, the surfactant has disordering poly-propylene-oxide (PPO) groups sandwiched between hydrophobic and hydrophilic groups, making it possible to achieve an extended membrane between water and oil with enhanced water-oil interaction. Without wishing to be bound by theory, since propylene oxide group is more hydrophobic than ethylene oxide group, it tends to dissolve more in the oil phase. This, in turn, will push the alkyl chain of surfactant further into oil phase. As a result, the interfacial layer between oil and water is extended and interfacial tension is reduced. In other words, more oil and water can be organised along the interface, and the mutual solubilization of water and triglycerides is enhanced.

x an integer between about 5 and about 30, thereby allowing for about 5 to about 30 PO-groups in the surfactant. Preferably, the surfactant has about 6 to about 20 PO-groups, and more preferably about 9 PO-groups to achieve the desired relative hydrophobicity.

EO is an ethylene oxide group (EO-group), and must follow the PO-group in the surfactant molecule in order to achieve the desired micro-emulsification effect.

y is an integer between about 5 and about 30, thereby allowing for about 5 to about 30 EO-groups in the surfactant molecule, preferably about 5 to counterbalance the relative hydrophobicity of the PO-group. For example, the larger the x, i.e. the more PO-groups, the larger the y needs to be, i.e., the more EO groups, in order to achieve the right balance of hydrophobicity to hydrophilicity. The ratio of x to y should be in the range of about 1:3 to about 3:1.

H is hydrogen.

Preferably, x is 9 and y is 5, so that the surfactant has the general formula B:

$$R\text{—}O\text{—}(PO)_9\text{—}(EO)_5\text{—}H \quad (B)$$

More preferably, x is 9 and y is 5, while R is an alkyl group having 8 carbon atoms, so that the surfactant has the formula C:

$$CH_3\text{—}(CH_2)_7\text{—}O\text{—}(PO)_9\text{—}(EO)_5\text{—}H \quad (C)$$

BLOCK POLYMER

Poly(Butadiene-b-Ethylene Oxide), a block polymer, is included in the inventive compositions to increase micro-emulsification efficiency. With the polymer, the amount of the relatively expensive surfactant in the composition may be reduced. With inclusion of the polymer, the compositions permit as low as about 1% surfactant and as high as about 40%, preferably about 12% to about 35%, and more preferably about 12% of the composition.

The poly-Butadiene chain has a molecular weight of about 1,000 to about 10,000, preferably, about 5,000. The poly-Ethylene Oxide chain has a molecular weight of about 1,000 to about 20,000, preferably, about 6,000.

Poly(Butadiene-b-Ethylene Oxide) suitable according to the present invention has a polydispersity, i.e. ratio of weight-average molecular weight to number-average molecular weight, of about 1 to about 5, preferably about 1 to about 1.05, and more preferably about 1.04. This low ratio insures a uniform distribution of the blocks which helps achieve the desired hydrophilic lipophilic balance.

About 0.01% to about 1% of poly(Butadiene-b-Ethylene Oxide) may be used in the inventive compositions, preferably about 0.1% to about 0.6%, and, more preferably, about 0.25% of the composition.

Cosmetically Acceptable Vehicle

Compounds of formula A and the block polymers employed in the inventive methods and compositions are liquid, and thus the invention is effective even in the absence of the carrier. However, the compositions according to the invention may comprise a cosmetically acceptable vehicle to act as a diluant, dispersant or carrier of compound A and polymer, so as to facilitate their distribution when the composition is applied to the skin.

The vehicle may be aqueous, anhydrous, a gel, or an emulsion. Preferably, the compositions are aqueous or an emulsion, especially water-in-oil or oil-in-water emulsion. Water when present will be in amounts which may range from 5 to 99%, preferably from 40 to 90%, optimally between 60 and 90% by weight.

Besides water, relatively volatile solvents may also serve as carriers within compositions of the present invention. Most preferred are monohydric $C_1$-$C_3$ alkanols. These include ethyl alcohol, methyl alcohol and isopropyl alcohol. The amount of monohydric alkanol may range from 1 to 70%, preferably from 10 to 50%, optimally between 15 and 40% by weight.

Emollient materials may also serve as cosmetically acceptable carriers. These may be in the form of silicone oils and synthetic esters. Amounts of the emollients may range anywhere from 0.1 to 50%, preferably between 1 and 20% by weight.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from 3 to 9, preferably from 4 to 5, silicon atoms. Linear volatile silicone materials generally have viscosities less than about 5 centistokes at 25° C. while cyclic materials typically have viscosities of less than about 10 centistokes. Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 25 million centistokes at 25° C. Among the preferred non-volatile emollients useful in the present compositions are the polydimethyl siloxanes having viscosities from about 10 to about 400 centistokes at 25° C.

Among the ester emollients are:
(1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.
(2) Ether-esters such as fatty acid esters of ethoxylated fatty alcohols.
(3) Polyhydric alcohol esters. Ethylene glycol mono- and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.
(4) Wax esters such as beeswax, spermaceti, myristyl myristate, stearyl stearate and arachidyl behenate.
(5) Sterol esters, of which cholesterol fatty acid esters are examples.

Fatty acids having from 10 to 30 carbon atoms may also be included as cosmetically acceptable carriers for compositions of this invention. Illustrative of this category are pelargonic, lauric, myristic, palmitic, stearic, isostearic, hydroxystearic, oleic, linoleic, ricinoleic, arachidic, behenic and erucic acids.

Humectants of the polyhydric alcohol type may also be employed as cosmetically acceptable carriers in compositions of this invention. The humectant aids in increasing the effectiveness of the emollient, reduces scaling, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol or sodium hyaluronate. The amount of humectant may range anywhere from 0.5 to 30%, preferably between 1 and 15% by weight of the composition.

Thickeners may also be utilized as part of the cosmetically acceptable carrier of compositions according to the present invention. Typical thickeners include crosslinked acrylates (e.g. Carbopol 982), hydrophobically-modified acrylates (e.g. Carbopol 1382), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Amounts of the thickener may range from 0.0001 to 5%, usually from 0.001 to 1%, optimally from 0.01 to 0.5% by weight.

Collectively, the water, solvents, silicones, esters, fatty acids, humectants and/or thickeners will constitute the cosmetically acceptable carrier in amounts from 1 to 99.9%, preferably from 80 to 99% by weight.

An oil or oily material may be present, together with an emulsifier to provide either a water-in-oil emulsion or an oil-in-water emulsion, depending largely on the average hydrophilic-lipophilic balance (HLB) of the emulsifier employed.

Additional Skin Benefit Agents

Various types of additional active ingredients may be present in cosmetic compositions of the present invention. Actives are defined as skin benefit agents other than emollients and other than ingredients that merely improve the physical characteristics of the composition. Although not limited to this category, general examples include anti-sebum ingredients such as talcs and silicas, anti-perspirant actives such as astringent salts, anti-aging actives such as retinoids, as well as alpha-hydroxy acids, beta-hydroxy acids, polyhydroxy acids, zinc salts, benzoyl peroxide, and sunscreens.

In hot and humid climates, facial sweat derived from eccrine glands can interact with sebum to amplify the perception of oily/greasy skin. Even in individuals with low-normal levels of sebum, sweat can interact with surface sebum to make an individual perceive their skin to be more oily. Therefore, cosmetic compositions that provide both control of sebum appearance and perception, as well as anti-perspirant benefits employ compounds of the general formula A and the specified block polymer, and further include astringent salts. In the present invention, the inclusion of antiperspirant compounds, in particular astringent salts, in a topical skin cream, reduces the perception of oily/greasy skin in the dermal areas having eccrine glands, especially face, arms, and legs. Thus, the perception of oily/greasy skin, especially facial skin, can be indirectly controlled by reducing the amount of facial sweating.

The astringent salts may be inorganic or organic salts of aluminum, zirconium, zinc and mixtures thereof. Preferably, the astringent salts are employed herein in particulate form, i.e., hydrophilic porous particles, of less than about 100 microns in size, preferably about 3 microns to about 10 microns in size. Salts useful as astringents or as components of astringent aluminum complexes include aluminum hydroxide, aluminum halides, aluminum hydroxyhalides, zirconyl oxyhalides, zirconyl hydroxyhalides and mixtures of these salt materials.

Aluminum salts of this type include aluminum chloride and the aluminum hydroxyhalides having the general formula $Al_2(OH)_xQ_y$—$XH_2O$ where Q is chlorine, bromine or iodine, where x is 2 to 5 and x+y=6 and x and y do not need to be integers; and where X is about 1 to 6. For example, aluminum chlorohydrate, having the formula $[Al_2(OH)_5Cl]$—$XH_2O$, is preferred, due to its ready commercial availability and relatively low cost.

Several types of complexes utilizing the above astringent salts are known in the antiperspirant art. For example, U.S. Pat. No. 3,792,068 (Luedders et al.), discloses complexes of aluminum, zirconium and amino acids such as glycine. Complexes reported therein and similar structures are commonly known as ZAG. The ZAG complexes ordinarily have an Al:Zr ratio of from about 1.67 to 12.5 and a Metal:Cl ratio of from about 0.73 to 1.93. The preferred amino acid for preparing such ZAG-type complexes is glycine of the formula $CH_2(NH_2)COOH$. Spherical ZAG, with particle size 1 to 100 microns, is especially preferred.

More specifically, the following is a list of astringent salts which may be useful for the present invention and which have approved listings under the United States Food & Drug Administration, Federal Register. They include aluminum chloride, aluminum chlorohydrate, aluminum chlorohydrex, aluminum chlorohydrex PEG, aluminum chlorohydrex PG, aluminum dichlorohydrate, aluminum dichlorohydrex PEG, aluminum dichlorohydrex PG, aluminum sesquichlorohydrate, aluminum sesquichlorohydrex PEG, aluminum sesquichlorohydrex PG, aluminum sulfate, aluminum zirconium octachlorohydrate, aluminum zirconium octachlorohydrex GLY (abbreviation for glycine), aluminum zirconium pentachlorohydrate, aluminum zirconium pentachlorohydrex GLY, aluminum zirconium tetrachlorohydrate, aluminum zirconium trichlorohydrate, aluminum zirconium tetrachlorohydrate GLY, and aluminum zirconium trichlorohydrate GLY.

Also suitable are:
potassium aluminium sulphate, also known as alum ($KAl(SO_4)_2 12H_2O$),
aluminium undecylenoyl collagen amino acid,
sodium aluminium lactate+aluminium sulphate $Al_2(SO_4)_3 + Na_2HAl(OOCCHOHCH_3)_2$—$(OH)_6$),
sodium aluminium chlorohydroxylactate,
aluminium bromohydrate ($Al_2Br(OH)_5 nH_2O$),
aluminium chloride ($AlCl_3 6H_2O$),
complexes of zinc salt and of sodium salt,
complexes of lanthanum and cerium, and
the aluminium salt of lipoamino acids (R—CO—NH—CHR'—CO—OAl—$(OH)_2$ with R=$C_6/C_{11}$ and R'=amino acid).

Preferably, the antiperspirant is an aluminium salt and, more preferably, it is chosen from potassium aluminium sulphate and aluminium chlorohydrate.

Amounts of the active astringent salt may range from about 0.000001% to about 20%, preferably from about 0.10% to about 18%, more preferably about 1 to about 15%, and optimally about 2% to about 3% by weight of the composition.

The inventive compositions may also include a retinoid. Retinoids increase collagen synthesis by dermal fibroblasts. This results in protection from sun damage and smoothening of wrinkled skin. The term "retinoids" as used herein includes retinoic acid, retinol, retinal, and retinyl esters. Included in the term "retinoic acid" are 13-cis retinoic acid and all-trans retinoic acid.

The term "retinol" as used herein includes the following isomers of retinol: all-trans-retinol, 13-cis-retinol, 11-cis-retinol, 9-cis-retinol, 3,4-didehydro-retinol. Preferred isomers are all-trans-retinol, 13-cis-retinol, 3,4-didehydro-retinol, and 9-cis-retinol. Most preferred is all-trans-retinol, due to its wide commercial activity.

Retinyl ester is an ester of retinol. The term "retinol" has been defined above. Retinyl esters suitable for use in the present invention are $C_1$-$C_{30}$ esters of retinol, preferably $C_2$-$C_{20}$ esters, and most preferably $C_2$, $C_3$, and $C_{16}$ esters because they are more commonly available. Examples of retinyl esters include but are not limited to: retinyl palmitate, retinyl formate, retinyl acetate, retinyl propionate, retinyl butyrate, retinyl valerate, retinyl isovalerate, retinyl hexanoate, retinyl heptanoate, retinyl octanoate, retinyl nonanoate, retinyl decanoate, retinyl undecandate, retinyl laurate, retinyl tridecanoate, retinyl myristate, retinyl pentadecanoate, retinyl heptadecanoate, retinyl stearate, retinyl isostearate, retinyl nonadecanoate, retinyl arachidonate, retinyl behenate, retinyl linoleate, retinyl oleate, retinyl lactate, retinyl glycolate, retinyl hydroxy caprylate, retinyl hydroxy laurate, retinyl tartarate.

The retinoids in the present invention are present in an amount of from 0.001% to 10%, preferably from 0.01% to 1%, and most preferably from 0.01% to 0.05%.

Beta-hydroxy acids include salicylic acid, for example. Zinc pyrithione is an example of zinc salts useful in the compositions of the present invention.

Sunscreens include those materials commonly employed to block ultraviolet light. Illustrative compounds are the derivatives of PABA, cinnamate and salicylate. For example, avobenzophenone (Parsol 1789®) octyl methoxycinnamate and 2-hydroxy4-methoxy benzophenone (also known as oxybenzone) can be used. Octyl methoxycinnamate and 2-hydroxy4-methoxy benzophenone are commercially available under the trademarks, Parsol MCX and Benzophenone-3, respectively. The exact amount of sunscreen employed in the compositions can vary depending upon the degree of protection desired from the sun's UV radiation.

Many cosmetic compositions, especially those containing water, must be protected against the growth of potentially harmful microorganisms. Anti-microbial compounds, such as triclosan, and preservatives are, therefore, necessary. Suitable preservatives include alkyl esters of p-hydroxybenzoic acid, hydantoin derivatives, propionate salts, and a variety of quaternary ammonium compounds. Particularly preferred preservatives of this invention are methyl paraben, propyl paraben, phenoxyethanol and benzyl alcohol. Preservatives will usually be employed in amounts ranging from about 0.1% to 2% by weight of the composition.

Use of the Novel Compounds and Compositions

The compositions according to the invention are intended primarily as a product for topical application to human skin, especially as an agent for controlling or preventing appearance or perception of excessive sebum secretion. Prevention of appearance and/or perception of sebum provides multiple benefits, including reduction of an unpleasant appearance and feel of greasy skin.

In use, a quantity of the composition, for example from 1 to 100 ml, is applied to exposed areas of the skin, from a suitable container or applicator and, if necessary, it is then spread over and/or rubbed into the skin using the hand or fingers or a suitable device.

The present invention also includes a cosmetic method of controlling or preventing an oily skin condition, or removing sebum secreted from sebocytes, especially in the facial area, by applying to the skin and/or removing from the skin the inventive composition. In another aspect, the present invention includes a cosmetic method of controlling, preventing, or treating oily or greasy hair.

In another aspect, the invention includes a method of controlling the sensory perception of sebum and sweat simultaneously, by micro-emulsifying sebum in the presence of sweat.

Product Form and Packaging:

The cosmetic skin composition of the invention can be in any form, e.g. formulated as a toner, gel, lotion, a fluid cream, or a cream. The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar. The invention accordingly also provides a closed container containing a cosmetically acceptable composition as herein defined.

The composition may also be included in capsules such as those described in U.S. Pat. No. 5,063,057.

EXAMPLES

The following specific examples further illustrate the invention, but the invention is not limited thereto.

The materials and methods used in the Examples are as follows.

Materials

Tri-block non-ionic surfactant, poly-oxy-propylene, poly-oxy-ethylene ether of octyl alcohol, (PEPOL A-638®), was obtained from Toho Chemical Industrial Co., Ltd., Japan. It has the general formula C:

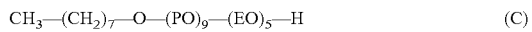

Poly(Butadiene-b-Ethylene oxide) was purchased from Polymer Source Inc., with molecular weight PBd(5000)—b—EO(6000) and Mw/Mn 1.04.

Poly-oxy-ethylene, poly-oxy-propylene block polymer (Pluronic F-38®) was obtained from BASF Corp., having generally the formula:

in which the average values of x, y and z are respectively 46, 16 and 46.

Triolein was purchased from Sigma-Aldrich Co., Milwaukee, Wis. and other chemicals used for making artificial sebum were obtained from Uniqema North America Co., Wilmington, Del. All chemicals were used as received.

Sebum

A modified model composition for liquid sebum was adapted from Strauss, et al., "Sebaceous Glands," *Physiology,* *Biochemistry and Molecular Biology of Skin*, Oxford University Press, New York (1991) and reported in the Table below.

TABLE 1

Composition of Model Sebum

| Components | Liquid sebum (MP 22 C.) % |
|---|---|
| Lauric Acid | 11.5 |
| Oleic acid | 11.5 |
| Isostearic acid | 5.75 |
| Tricaprin | 11.5 |
| Triolein | 11.5 |
| Glycerol Triisostearate | 5.75 |
| Oleyl Oleate | 10.4 |
| Myristyl Myristate | 10.4 |
| Isostearyl isostearate | 5.2 |
| Squalene | 12 |
| Cholesterol Oleate | 3 |
| Cholesterol | 1.5 |

Methods

Micro-emulsion phase equilibria were determined by visual inspection of samples made up in stoppered 15 ml flask tube, thermostate to ±0.1 C. The samples are weighed into test tube and sealed. At constant sample composition and as a function of temperature, the occurring phases are characterized by visual inspection in both transmitted and scattered light, using crossed polarizers to determine the presence of the lamellar phase. Phase behaviors of ternary systems were studied by taking a vertical section through the phase prism at constant oil/water ratio at one and the phase diagrams were monitored as a function of surfactant concentrations.

Example 1

This example demonstrates the role of surfactant structure on micro-emulsification.

Several nonionic surfactants which are relatively comparable to triolein in alkyl chain length were pre-screened. A single chain oleyl glycol (Oleyl $EO_6$) and a double chain oleyl glycol (Dioleyl $EO_{22}$) were tested for their efficacy to micro-emulsify triolein oil. It was found that their ability to solubilize triolein is quite low. Only about 20% triolein can be dissolved in these surfactant systems.

In comparison, the tri-block non-ionic surfactant, poly-oxypropylene, poly-oxyethylene ether of octyl alcohol, PEPOL A-638, has been selected for its micro-emulsification efficacy of triglycerides. This surfactant has disordering polypropylene oxide (PPO) groups sandwiched between hydrophobic and hydrophilic groups. The structure makes it possible to achieve an extended membrane between water and oil with enhanced water-oil interaction. In this study, triolein was used as base component for sebum mixtures. The phase behavior of triolein-water mixture with tri-block surfactant is shown in the Table below. When plotted as a phase diagram of a function of Surfactant Concentration versus Temperature, a typical "fish" style diagram with only "fish tail" is observed. The efficiency of amphiphilic surfactant is usually represented by the minimum weight fraction of amphiphile needed to obtain a homogeneous solution of equal masses of water and oil.

It can be seen from the Table below that only about 19% to about 20% tri-block surfactant is needed to micro-emulsify triolein and water at 1:1 weight ratio.

TABLE 2

| Temperature, Deg. C. | Surfactant concentration w. % (PEPOL A-638) | | | |
|---|---|---|---|---|
| | 20% | 25% | 30% | 35% |
| At lower boundary for single phase | 47.5 | 42.2 | 36.9 | 31.2 |
| At higher boundary for single phase | 50.1 | 50.2 | 50.7 | 52.1 |
| At lower boundary for lamellar phase | X | 44.5 | 39.8 | 34 |
| At higher boundary for lamellar phase | X | 45.6 | 45.5 | 45.4 |

Therefore, the tri-block surfactants according to the present invention have the necessary structure to efficiently micro-emulsify triolein, an important component of sebum.

Example 2

This is a comparative example, demonstrating the role of polymer structure on micro-emulsification.

To further understand the role of different polymers on the formation of micro-emulsion, two different types of block polymers, both amphiphilic surface actives, were studied to explore their ability to boost micro-emulsification efficacy. The results are shown in the Tables below.

A small amount of $(EO)_x$—$(PO)_y$—$(EO)_z$ block polymer (PLURONIC F—38 brand) was added to the surfactant phase. PLURONIC F—38 block polymer has two long hydrophilic EO ($x=z=46$) blocks at the each end of the polymer and has a relatively short PO block ($y=16$) in between.

It can be seen in the Table below that adding 2% and 4% PLURONIC F—38 polymer in tri-block surfactant phase has no effect on micro-emulsification efficacy of triolein.

TABLE 3

| Temperature, Deg. C. | | Surfactant concentration w. % | | | | | |
|---|---|---|---|---|---|---|---|
| | | 20% | 22.5% | 25% | 27.5% | 30% | 35% |
| Tri-block surfactant only | At lower boundary for single phase | 44.5 | | 42.2 | | 36.9 | 31.2 |
| | At higher boundary for single phase | 50.1 | | 50.2 | | 50.7 | 52.1 |
| 2% Pluronic F38 in surfactant phase | At lower boundary for single phase | 48.7 | 46.75 | 43 | 40.75 | | |
| | At higher boundary for single phase | 50.25 | 50.25 | 50.1 | 50.25 | | |
| 4% Pluronic F38 in surfactant phase | At lower boundary for single phase | 49.4 | 47.75 | 44 | 41.25 | | |
| | At higher boundary for single phase | 51 | 50.75 | 50.5 | 50.75 | | |

On the other hand, adding 2% amphiphilic block polymer Poly(Butadiene-b-Ethylene oxide) in tri-block surfactant phase (PEPOL A—638 system), i.e., to replace 2% of the surfactant, will enhance micro-emulsification efficacy significantly, and the surfactant required to micro-emulsify triolein is reduced to about 15% (Table below) from the about 20% needed in the absence of polymer. But further increase block polymer Poly(Butadiene-b-Ethylene oxide) beyond 2% (relative to amount of surfactant) will not further increase micro-emulsification efficacy for studied system.

TABLE 4

| Temperature, Deg. C. | | Surfactant concentration w. % | | | | |
|---|---|---|---|---|---|---|
| | | 15 | 20 | 25 | 30 | 35 |
| Tri-block surfactant only | At lower boundary for single phase | X | 47.5 | 42.2 | 36.9 | 31.2 |
| | At higher boundary for single phase | X | 50.1 | 50.2 | 50.7 | 52.1 |
| **2% poly(Butadiene-b-EO) in surfactant phase | At lower boundary for single phase | 50 | 43.5 | 40.3 | 35.5 | 29.4 |
| | At higher boundary for single phase | 51.8 | 50.8 | 51.9 | 52.5 | 53.6 |

**On a weight basis as a percent of the overall composition, for each of the 15-35% surfactant concentrations listed in the Table, the percentages are: 0.3%, 0.4%, 0.5%, 0.6%, and 0.7% polymer, respectively.

Example 3

This example illustrates sebum micro-emulsification in accordance with the present invention.

Artificial sebum was made based on the composition presented in Table 1. Using this sebum composition as the oil phase, a ternary phase diagram of sebum, water and non-ionic surfactant with 2% block polymer added to the surfactant phase was studied and the results are shown in the Table below.

TABLE 5

| Temperature, Deg. C. | | Surfactant concentration w. % | | | | |
|---|---|---|---|---|---|---|
| | | 15% | 20% | 25% | 30% | 35% |
| Artificial sebum | At lower boundary for single phase | 21.7 | 20.4 | 20.9 | 19.3 | 18.2 |
| | At higher boundary for single phase | 24.7 | 28.3 | 31.6 | 34.2 | 37.2 |
| Triolein only | At lower boundary for single phase | 50 | 43.5 | 40.3 | 35.5 | 29.4 |
| | At higher boundary for single phase | 51.8 | 50.8 | 51.9 | 52.5 | 53.6 |

Example 5

The data in the Table below demonstrate the micro-emulsification efficacy of different surfactant-polymer combinations.

TABLE 6

| Surfactant system | Oil system | Efficacy (minimum surfactant concentration for 1:1 oil-water ratio) |
|---|---|---|
| Tri-block surfactant only | Triolein | 20% |
| Tri-block surfactant + PLURONIC F38 | Triolein | 20% |
| Tri-block surfactant + Poly(Butadiene-b-EO) | Triolein | 15% |
| Tri-block surfactant + Poly(Butadiene-b-EO) | Sebum | 12% |

The data show that PLURONIC F38 has no effect on improving the micro-emulsification efficacy of triolein, while Poly(Butadiene-b-EO) increases the micro-emulsification efficacy of the tri-block surfactant system for both triolein and sebum.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention. Throughout this application, various publications have been cited. The entireties of each of these publications are hereby incorporated by reference herein.

What is claimed is:

1. A skin care cosmetic composition comprising:
   (i) about 1% to about 40% of a compound having the formula A:

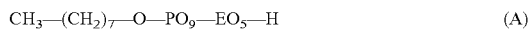
   $$CH_3-(CH_2)_7-O-PO_9-EO_5-H \qquad (A)$$

wherein:
   O is an oxygen atom;
   PO is a propylene oxide group;
   EO is an ethylene oxide group;
   (ii) about 0.1% to about 0.6% of poly(Butadiene-Ethylene Oxide) wherein said poly-Butadiene chain has a molecular weight of about 1,000 to about 10,000; and wherein said poly-Ethylene Oxide chain has a molecular weight of about 1,000 to about 20,000; and
   (iii) a cosmetically acceptable vehicle;
   wherein the composition forms a micro-emulsion with sebum.

2. The skin care cosmetic composition of claim 1 wherein the compound of formula A comprises about 12% to about 35% of said composition.

3. The skin care cosmetic composition of claim 1 wherein the compound of formula A comprises about 12% of said composition.

4. The skin care cosmetic composition of claim 1 wherein said poly(Butadiene-b-Ethylene Oxide) has a polydispersity of about 1.04.

5. The skin care cosmetic composition of claim 1 wherein the poly(Butadiene-b-Ethylene Oxide) comprises about 0.25% of said composition.

6. The composition of claim 1, further comprising an astringent salt.

7. The composition of claim 6, wherein said astringent salt is selected from the group consisting of aluminum hydroxide, aluminum halides, aluminum hydroxyhalides, zirconyl oxyhalides, zirconyl hydroxyhalides and mixtures thereof.

8. The skin care cosmetic composition of claim 6, wherein said astringent salt is selected from the group consisting of an aluminum salt having the general formula $Al_2(OH)_xQ_y \cdot XH_2O$; wherein Q is chlorine, bromine or iodine; wherein x is 2 to 5 and x+y=6 and x and y do not need to be integers; and wherein X is about 1 to about 6.

9. The skin care cosmetic composition of claim 6, wherein said astringent salt is selected from the group consisting of aluminum chloride, aluminum chlorohydrate, aluminum chlorohydrex, aluminum chlorohydrex PEG, aluminum chlorohydrex PG, aluminum dichlorohydrate, aluminum dichlorohydrex PEG, aluminum dichlorohydrex PG, aluminum sesquichlorohydrate, aluminum sesquichlorohydrex PEG, aluminum sesquichlorohydrex PG, aluminum sulfate, aluminum zirconium octachlorohydrate, aluminum zirconium octachlorohydrex GLY, aluminum zirconium pentachlorohydrate, aluminum zirconium pentachlorohydrex GLY, aluminum zirconium tetrachlorohydrate, aluminum zirconium trichlorohydrate, aluminum zirconium tetrachlorohydrate GLY, and aluminum zirconium trichlorohydrate GLY, and mixtures thereof.

10. The skin care cosmetic composition of claim 1, wherein said composition is a leave-on composition.

11. A cosmetic method of microemulsifying sebum by applying to the skin the composition of claim 1.

* * * * *